US012773343B2

(12) United States Patent
Maaskamp et al.

(10) Patent No.: US 12,773,343 B2
(45) Date of Patent: Oct. 27, 2026

(54) OPTIONAL SHAPED RECTOCELE PADDLES

(71) Applicant: MEDICELE LLC, Scottsdale, AZ (US)

(72) Inventors: Ryan Maaskamp, Scottsdale, AZ (US); Armand Maaskamp, Scottsdale, AZ (US)

(73) Assignee: SURGIN, INC., Scottsdale, AZ (US)

( * ) Notice: Subject to any disclaimer, the term of this patent is extended or adjusted under 35 U.S.C. 154(b) by 123 days.

(21) Appl. No.: 18/591,105

(22) Filed: Feb. 29, 2024

(65) Prior Publication Data

US 2024/0197522 A1 Jun. 20, 2024

Related U.S. Application Data

(63) Continuation of application No. 18/094,323, filed on Jan. 6, 2023, now Pat. No. 11,951,034, which is a continuation of application No. 17/850,091, filed on Jun. 27, 2022, now Pat. No. 11,596,542.

(51) Int. Cl.
*A61F 6/12* (2006.01)

(52) U.S. Cl.
CPC .................................... *A61F 6/12* (2013.01)

(58) Field of Classification Search
CPC .. A61F 6/12; A61F 5/0093; A61F 6/06; A61F 6/20; A61F 6/00; A61F 6/14; A61F 6/146; A61F 6/16; A61M 29/02; A61B 17/02; A61B 17/42; A61B 2017/00805; A61B 2017/00424; A61B 2017/0046; A61B 2017/00473
See application file for complete search history.

(56) References Cited

U.S. PATENT DOCUMENTS

| | | | | |
|---|---|---|---|---|
| 6,758,826 B2 * | 7/2004 | Luettgen | ............ | A61H 23/0254 601/72 |
| 7,771,344 B2 | 8/2010 | Ziv | | |
| 7,981,024 B2 | 7/2011 | Levy | | |
| 8,302,608 B2 | 11/2012 | Harmanli | | |
| 8,360,954 B2 | 1/2013 | Kim | | |
| 11,259,957 B2 | 3/2022 | Maaskamp et al. | | |
| 2003/0069476 A1 | 4/2003 | Deslauriers et al. | | |
| 2013/0053627 A1 | 2/2013 | Bercovich | | |
| 2014/0243584 A1 | 8/2014 | Bercovich | | |
| 2014/0261445 A1 | 9/2014 | Maaskamp et al. | | |
| 2016/0331407 A1 * | 11/2016 | Anderson | .............. | A61B 17/02 |
| 2017/0100278 A1 | 4/2017 | Ziv et al. | | |

* cited by examiner

*Primary Examiner* — Ophelia A Hawthorne
(74) *Attorney, Agent, or Firm* — Kenneth Altshuler

(57) ABSTRACT

A rectocele device having a rectocele handle with a first paddle removably affixed to a rectocele paddle connector at a paddle connector end. A second paddle is configured to replace the first paddle after the first paddle is removed from the rectocele paddle connector. The first paddle is configured and sized to fit within a human vagina wherein the first paddle is only removable from the handle distal end when the first paddle is not deployed in the human vagina. The first paddle is shaped differently from the second paddle. The first or second paddle is inserted in a human vagina (by a woman using the rectocele device) wherein the first or second paddle can be leveraged against a rectocele via the rectocele handle thereby pushing the rectocele bulge back into the colon so that the woman can evacuate a bowel more efficiently.

19 Claims, 10 Drawing Sheets

OPTIONAL SHAPED RECTOCELE PADDLES

CROSS-REFERENCE TO RELATED APPLICATIONS

This application is a continuation patent application claiming priority to and the benefit of patent application Ser. No. 18/094,323, entitled Optional Shaped Rectocele Paddles filed Jan. 6, 2023, the entire disclosure of which is hereby incorporated by reference, which is a continuation patent application claiming priority to and the benefit of patent application Ser. No. 17/850,091, entitled Optional Shaped Rectocele Paddles filed Jun. 27, 2022.

FIELD OF THE INVENTION

The present invention is directed to a rectocele device that is useful in reducing the effects of rectoceles in women.

BACKGROUND OF THE INVENTION

A rectocele is a herniation (bulge) of the front wall of the rectum into the back wall of the vagina. The tissue between the rectum and the vagina is known as the rectovaginal septum, which can become thin and weak over time resulting in a rectocele. When rectoceles are small, most women have no symptoms. However, when a rectocele becomes large, a woman's rectum can balloon into her vagina, which can be exacerbated during a bowel movement as shown in FIG. 1A. As a result, the woman may experience the sensation of pressure or protrusion within the vagina, as well as the occasional feeling that the rectum has not been completely emptied after a bowel movement. In more moderate cases, a woman may have difficulty passing stool because the attempt to evacuate pushes the stool into the rectocele instead of out through the anus.

In an attempt to aid with a bowel movement in cases of rectocele, a woman may insert her fingers into her vagina to manually press against the rectocele, which helps create a uniform pathway for stool to move out of the rectum. Because a rectocele may protrude to the right or left of the posterior wall of the vagina, by using the sense of touch in her fingers, a woman is able to reposition her fingers to where the rectocele occurs. In other words, a woman is able to press against the rectocele with her fingers by taking advantage of biofeedback in her fingers.

Though surgical procedures exist to repair rectoceles and cystoceles, in less severe cases, a number of optional devices currently exist to provide some rectocele and/or cystocele relief. One family of devices includes unitary spoon-like instruments that are typically metal or hard plastic, which are used to assist in a bowel movement just prior to having the bowel movement and then is withdrawn after the bowel movement.

Another family of devices used to address rectoceles includes pessaries, which are typically inflated balloons that provide static pressure on all surfaces of the vaginal canal (the rectovaginal wall, lateral walls and the bladder-vaginal wall). Pessaries offer extended support to address rectoceles. Unlike a spoon for assisting in a bowel movement, pessaries are not inserted into a vagina just prior to a bowel movement and then removed at the point of when a bowel movement is complete, or prior to the point of urination and then removed just when/after urination is complete. Rather, pessaries are left in the vagina for an extended period of time, sometimes being inserted in the morning and removed at night or even to being left in for days at a time, if not longer. Moreover, due to the static nature of pessaries, pessaries are unable to be manipulated to push prolapsing organs back into place once inserted in a vagina. It is believed that any device like a pessary left inside of a vagina (even pessary-like devices that are detached from an insertion handle, deployed inside of a vagina and left there beyond a minute or two before a bowel movement to just after a bowel movement) are suboptimal or otherwise dissatisfactory.

Still another family of devices includes expanding paddles or expanding pessaries that are contracted (small) when inserted in a woman's vagina and then expanded to a larger size once inserted or otherwise deployed in a woman's vagina. In this way, the woman's vaginal cavity is enlarged due to the expanded paddle, the expanded paddle is then pressed against the rectocele. Examples of expanding paddles includes balloon paddles or paddles with linkages that expand inside of a sheath or some other covering. One downside to these 'non-static' paddles is complexity of design and active expansion by the woman using the expanding paddle devices. In other words, a woman must perform the operation of expanding the paddle all while trying to move a bowel.

It is to innovations related to addressing passing a bowel movement in women suffering from a rectocele that the claimed invention is generally directed.

SUMMARY OF THE INVENTION

The present invention is directed to a rectocele/cystocele device that is useful in providing pressure against the rectocele to improve bowel movements in women or against the cystocele to improve urination events in women.

In that light, one embodiment of the present invention can therefore comprise a rectocele device that has a rectocele handle attached to one of several optionally different shaped rectocele paddles. In more detail, the rectocele device can comprise a rectocele handle that is essentially defined between a proximal handle end and a handle distal end and a rectocele paddle connector located at the handle distal end. The rectocele device includes a first static paddle removably affixed to the rectocele paddle connector at a paddle connector end. A second static paddle is configured to replace the first static paddle after the first static paddle is removed from the rectocele paddle connector. The first static paddle is configured and sized to fit within a human vagina wherein the first static paddle is only removable from the handle distal end when the first static paddle is not deployed in the human vagina.

Yet another embodiment of the present invention can therefore include a rectocele managing instrument generally comprising a rectocele handle attached to one of several optionally different shaped rectocele paddles. In this embodiment, the rectocele handle can be gripped by a user's hand, the handle being defined as a rigid or semi-rigid member that extends between a handle proximal end and a handle distal end, a rectocele paddle connector located at the handle distal end. The rectocele device further comprises a second static paddle that is affixed to the rectocele paddle connector, the second static paddle is a replacement of a first static paddle that was affixed to the rectocele paddle connector prior to the second static paddle being connected thereto. The first static paddle is shaped differently than the second static paddle. The first static paddle and the second static paddle are configured to fit within a human vagina. The first and the second static paddles are only removable from the handle distal end when not deployed in the human vagina.

Still yet another embodiment of the present invention can therefore comprise a method that uses a rectocele handle essentially defined as a member that is between a proximal handle end and a handle distal end and having a rectocele paddle connector located at the handle distal end. The method steps include unlocking a first static paddle from the rectocele paddle connector, the first static paddle is removed from the rectocele handle, and a second static paddle is engaged with (on) the rectocele paddle connector. The second static paddle comprises a different paddle geometry than the first static paddle. After the second static paddle is engaged with the rectocele paddle connector, the second static paddle is locked in a non-rotational relationship to the rectocele paddle connector. A non-rotational relationship means that when the second static paddle is engaged with the rectocele paddle connector and locked in place, the second static paddle cannot rotate (with relation to the rectocele paddle connector). With the rectocele device assembled, next the second static paddle is inserted in a human vagina (by a woman using the rectocele device) but not the rectocele handle in the human vagina. When in the human vagina, the second static paddle can be leveraged against a rectocele via the rectocele handle thereby pushing the rectocele bulge back into the colon so that the woman can evacuate the bowel more efficiently. The first static paddle is shaped differently from the second static paddle.

DETAILED DESCRIPTION

Figure 1A:
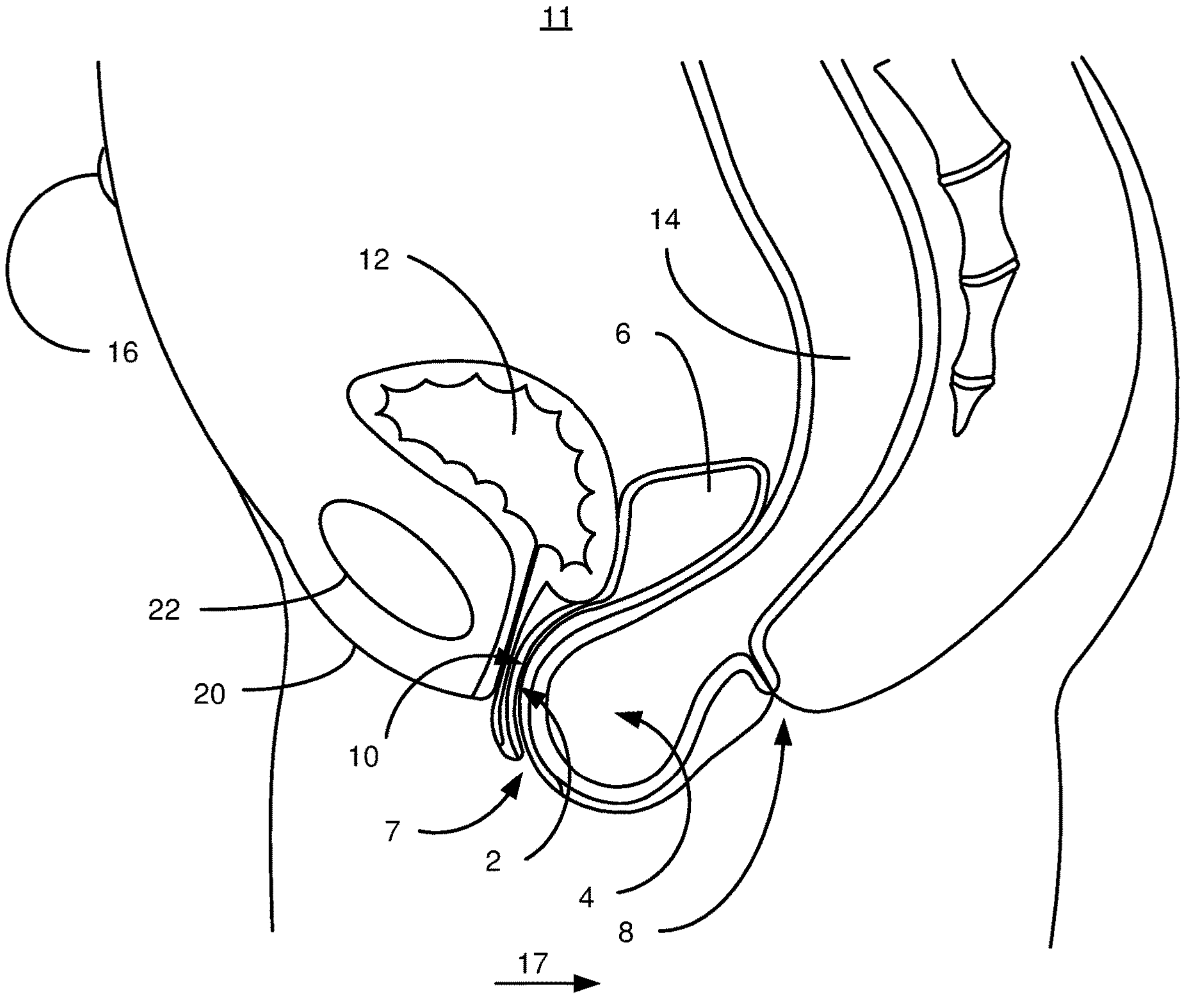
FIG. 1A is a line drawing that illustratively depicts a cross section of a pelvic area of a woman suffering from a rectocele.

Initially, this disclosure is by way of example only, not by limitation. Thus, although the instrumentalities described herein are for the convenience of explanation, shown and described with respect to exemplary embodiments, it will be appreciated that the principles herein may be applied equally in other similar configurations involving holding back rectoceles. The phrases "in one embodiment", "according to one embodiment", and the like, generally mean the particular feature, structure, or characteristic following the phrase, is included in at least one embodiment of the present invention and may be included in more than one embodiment of the present invention. Importantly, such phases do not necessarily refer to the same embodiment. If the specification states a component or feature "may", "can", "could", or "might" be included or have a characteristic, that particular component or feature is not required to be included or have the characteristic. As used herein, the terms "having", "have", "including" and "include" are considered open language and are synonymous with the term "comprising". Furthermore, as used herein, the term "essentially" is meant to stress that a characteristic of something is to be interpreted within acceptable tolerance margins known to those skilled in the art in keeping with typical normal world tolerance, which is analogous with "more or less." For example, essentially flat, essentially straight, essentially on time, etc. all indicate that these characteristics are not capable of being perfect within the sense of their limits. Accordingly, if there is no specific +/− value assigned to "essentially", then assume essentially means to be within +/−2.5% of exact. The term "connected to" as used herein is to be interpreted as a first element physically linked or attached to a second element and not as a "means for attaching" as in a "means plus function". In fact, unless a term expressly uses "means for" followed by the gerund form of a verb, that term shall not be interpreted under 35 U.S.C. § 112(f). In what follows, similar or identical structures may be identified using identical callouts.

Some aspects of the present invention are directed to a rectocele device having a rectocele handle with a first static paddle removably affixed to a rectocele paddle connector at a paddle connector end. A second static paddle is configured to replace the first static paddle after the first static paddle is removed from the rectocele paddle connector. The first static paddle is configured and sized to fit within a human vagina wherein the first static paddle is only removable from the handle distal end when the first static paddle is not deployed in the human vagina. The first static paddle is shaped differently from the second static paddle. The first or second static paddle is inserted in a human vagina (by a woman using the rectocele device) wherein the first or second static paddle can be leveraged against a rectocele via the rectocele handle thereby pushing the rectocele bulge back into the colon so that the woman can evacuate the bowel more efficiently. The differently shaped static paddles provides advantages for a woman using the rectocele device in that a woman can select a static paddle that feels or works best for her body. She may also select a rotational angle when locking the static paddle to the rectocele handle to improve leverage for specific needs.

FIG. 1A depicts a cross section of a pelvic area of a woman 11 suffering from a rectocele 4 thereby illustrating an exemplary environment in which embodiments of the present invention can be practiced. The rectocele 4 is shown bulging into the rectovaginal wall 2 of the vagina 6. The rectovaginal wall 2 is the septum between the vaginal vault (vagina) 6 and the rectal vault (rectum) 14 in the posterior direction 17 of the vagina 6. For reference, also shown herein, are the bladder 12, the bladder-vaginal wall 10, the vaginal opening 7, and the anus 8. Though not shown, the vagina 6 also has lateral walls of the vagina 6, which directionally extend towards the inner thighs of the woman 11. In other words, the rectovaginal wall 2 extends towards the posterior 17 and the bladder-vaginal wall 10 extends towards the anterior (pubic bone 22) of the woman 11, whereas the lateral walls of the vagina 6 are orthogonal to the anterior/posterior direction. From the anterior side, also shown are the belly button 16, the pubic bone 22, and the mons veneris 20.

Figure 1B:
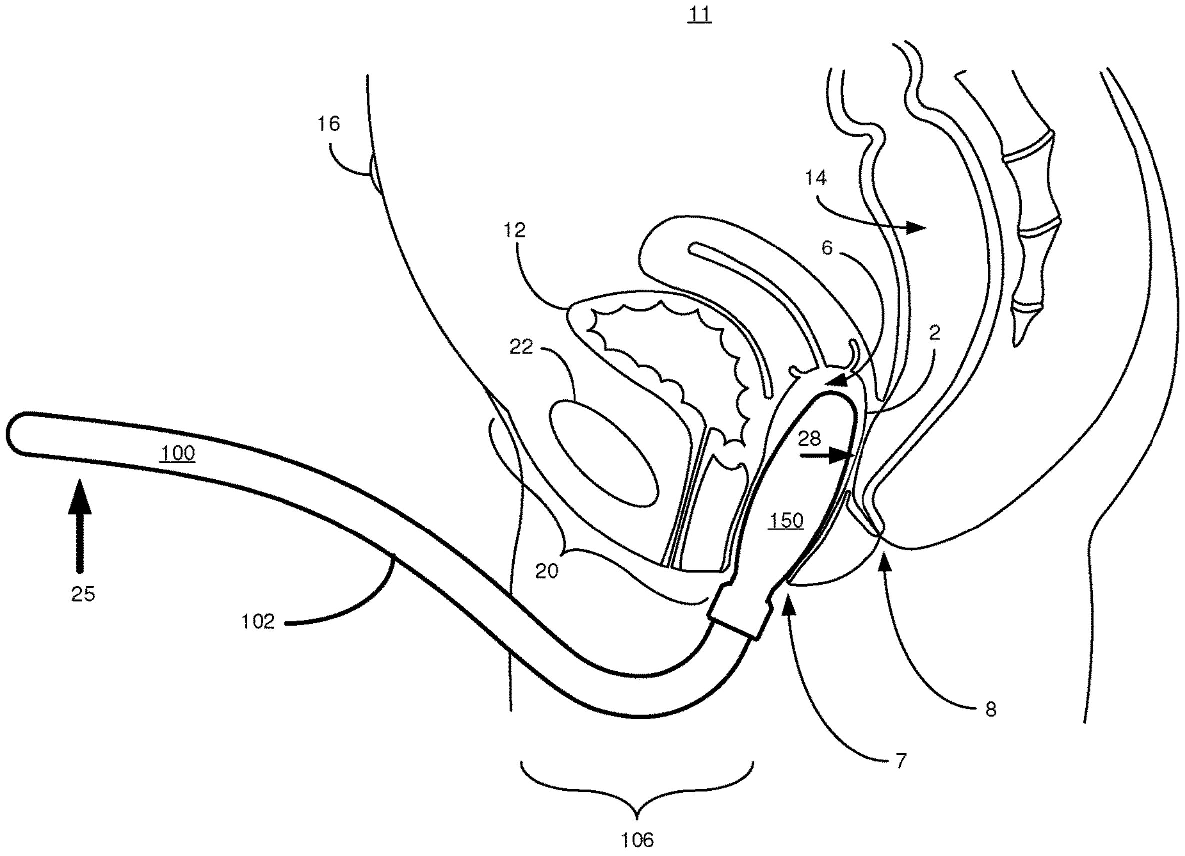
FIG. 1B is a line drawing of a rectocele device embodiment managing the rectocele of FIG. 1A consistent with embodiments of the present invention.

FIG. 1B is a line drawing of a rectocele device embodiment managing the rectocele 4 of FIG. 1A consistent with embodiments of the present invention. As illustratively shown, with the paddle 150 is inserted in the vagina 6, the rectocele handle 102 (which is grasped by a woman 11 using the rectocele device 100) is levered/rotated towards the belly button 16 (as shown by arrow 25). More specifically, as the rectocele handle 102 is pulled towards the belly button 16, the rectocele handle 102 pivots about the mons veneris 20. In this way, the rectocele 4 of FIG. 1A is manually pressed back towards the rectal vault 14 (see arrow 28) thereby reducing or eliminating the rectocele bulge 4 so that the woman 11 can better complete her bowel movement. As shown, the rectocele device's arched distal neck 106 is essentially outside of the vaginal opening 7. In other words, in certain embodiments, the rectocele handle 102 is not intended to go into the vagina 6.

Figure 2:
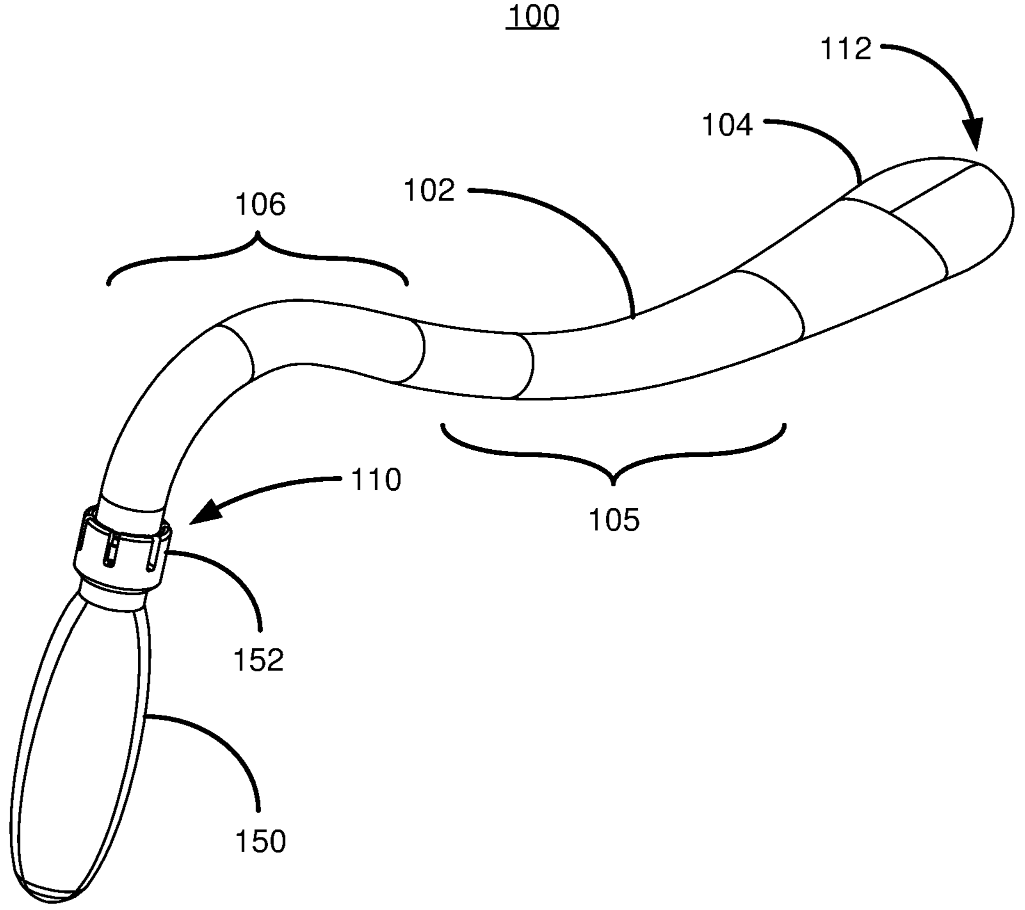
FIG. 2 is an isometric view line drawing of a rectocele device consistent with embodiments of the present invention.

FIG. 2 is an isometric view line drawing of a rectocele device 100 consistent with embodiments of the present invention. The main components shown include a rectocele handle 102 connected to a removable paddle 150, which is one of at least two differently shaped paddles. This handle embodiment 102 is "S" shaped with a concave dip 105 between the handle proximal end 112 and the arched distal neck 106, which is opposite to the curvature of the concave dip 105. The concave dip 105 provides an improved grip (when held by a user/woman with a rectocele 4) and leverage of the first static paddle 150 when being used against a rectocele 4, however other embodiments contemplate no concave dip between the arched distal neck 106 and the handle proximal end 112. In this embodiment, the handle 102 further comprises a flared proximal handle region 104 that terminates into the handle proximal end 112 to improve a user's grip and leverage during use. However, other embodiments do not envision a flared proximal handle region 104, whatsoever. The handle distal end 110 is configured to matingly engage with a paddle connector 152 on the paddle 150 which fixedly connects the removable paddle 150 to the rectocele handle 102 when in an orientation that is locked in place.

Figure 3:
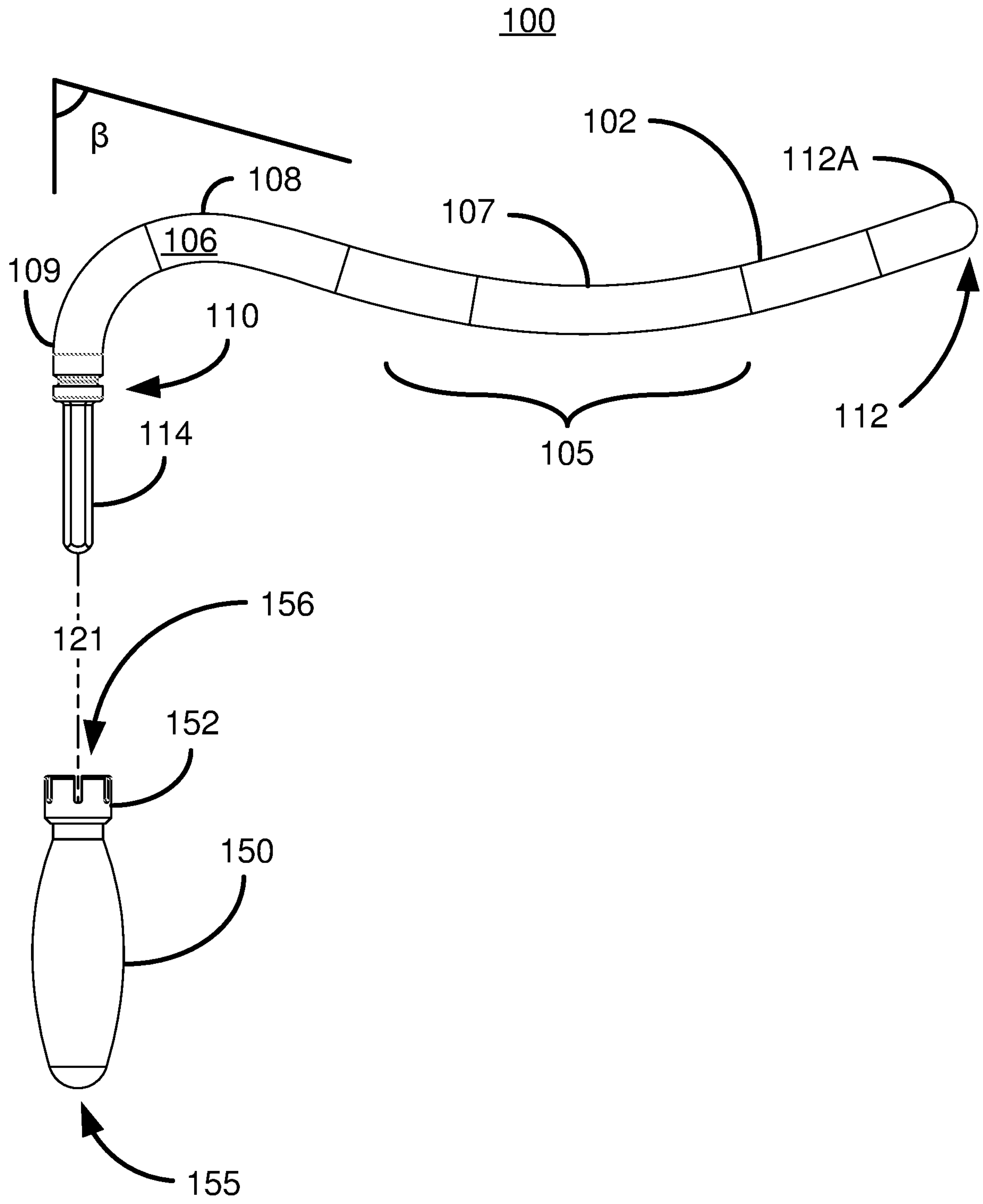
FIG. 3 is a side view line drawing of the rectocele device embodiment with the removable paddle 150 that is shown detached from the rectocele handle consistent with embodiments of the present invention.

FIG. 3 is a side view line drawing of the rectocele device embodiment 100 with the removable paddle 150 that is shown detached from the rectocele handle 102 consistent with embodiments of the present invention. With respect to the handle 102, the arched distal neck apex 108 is essentially horizontally in-line with the top of the handle proximal end top surface 112A. In other words, the arched distal neck apex 108 and the handle proximal end top surface 112A define a horizontal line in this embodiment. Accordingly, the arched distal neck apex 108 (and therefore also the handle proximal end top surface 112A) has essentially a 90° angle relationship with the outer handle distal end 109. Furthermore, the outer handle distal end 109 comprises a less than 90° angle relationship β with the outer inflection point 107 of the concave dip 105.

In this embodiment, the handle 102 is configured to join the static paddle 150 via a peg 114 that extends from the handle distal end 110, as shown. The peg 114 is configured and arranged to insert into a paddle aperture 156 that is located at the paddle connector 152. The paddle aperture 156 leads into a channel/cavity 154 (shown in FIG. 5), as indicated by the dashed line 121. The paddle connector 152 comprises expansion slots 158 that permit the paddle connector 152 to elastically expand outwardly to receive the handle distal end 110 (and then snap back essentially into the paddle connector's original shape to clamp over the handle distal end 110). In this embodiment, the static paddle terminal end 155 is rounded for easy insertion into a vagina 6.

Figure 4A:
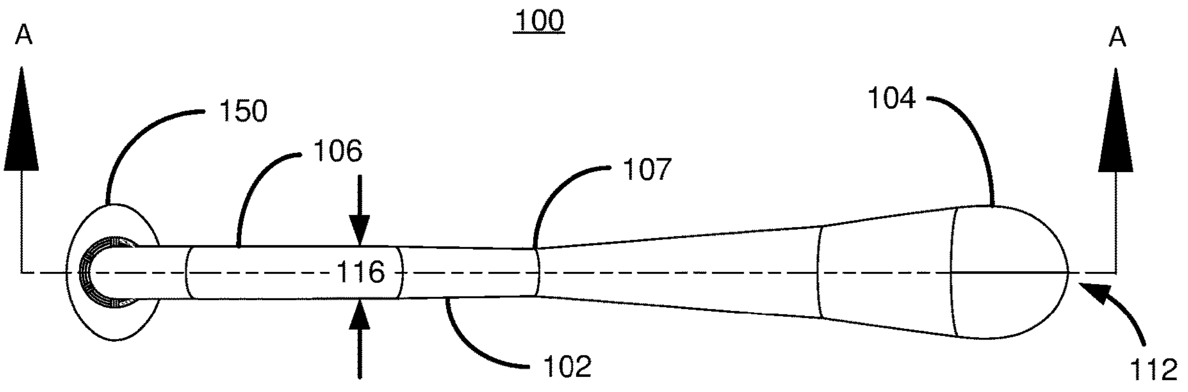
FIG. 4A is a top view line drawing of the rectocele device consistent with embodiments of the present invention.

FIG. 4A is a top view line drawing of the rectocele device 100 consistent with embodiments of the present invention. In the present embodiment, the handle width 116 from the handle distal end 110 to the outer inflection point 107 is essentially uniform along the sides. The handle width 116 flares from the outer inflection point 107 to the flared proximal handle region 104 at the handle proximal end 112. Some embodiments contemplate the width 116 narrowing between the arched distal neck 106 and the outer inflection point 107, wherein the outer inflection point 107 is narrower than the arched distal neck 106. In this embodiment, the static paddle 150 is elliptically shaped with the longest radius in the direction of the handle width 116. A cross-section cut-line A-A is illustratively drawn along the center axis (top view) of the rectocele device 100.

Figure 4B:
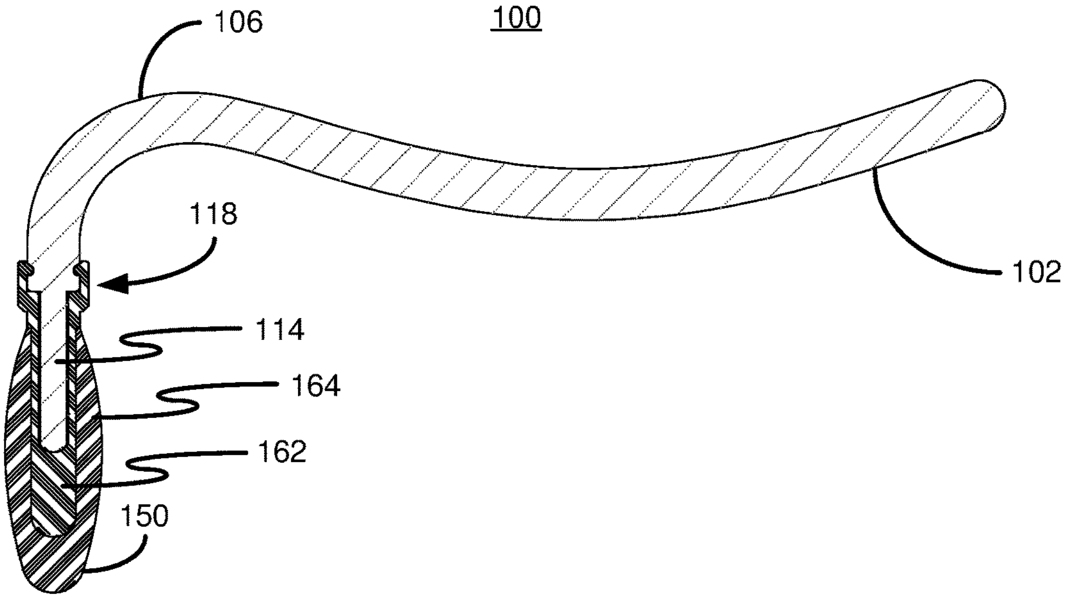
FIG. 4B is a cross-section line drawing along cut-line A-A (of FIG. 4A) of the rectocele device consistent with embodiments of the present invention.

FIG. 4B is a cross-section line drawing along cut-line A-A (of FIG. 4A) of the rectocele device 100 consistent with embodiments of the present invention. In this embodiment, the handle 102 and the peg 114 are a single element/unit. The handle 102 and the peg 114 can be a stiff molded polymer, metal, composite or some other material that provides adequate stiffness to lever the rectocele device 100 counter-clockwise against a rectocele 4. Other embodiments envision the peg 114 being fixedly attached to the handle 102 in a relationship wherein the peg 114 and the handle 102 are together sufficiently stiff to provide adequate leverage to manipulate or otherwise press into a rectocele 4.

In this arrangement, the static paddle 150 is removably fixed to the handle distal end 110 via the rectocele paddle connector 118. The term 'static paddle' is defined herein as a rectocele paddle that comprises a paddle volume that essentially cannot be increased, such as by some internal mechanical lever or balloon, for example. Hence, a static paddle essentially comprises a constant volume that may compress or physically change slightly due to compressive effects of the materials used in the static paddle, such as air, foam, gel, rubber, etc. Compression may occur when the static paddle 150 is used inside of a vagina 6 to manage a rectocele. Slight effects of thermal expansion due to body heat are not considered an outside/manual force intended to increase the volume of a static paddle 150 in a way that would depart from the definition of 'static paddle' because thermal expansion is not manually expanding a paddle in any appreciable way like some internal mechanical lever or balloon, for example.

The static paddle 150 embodiment comprises a flexible overmold 164 and a stiff (inner) core or armature 162. In certain embodiments, the stiff core 162 includes the snap ring 160, the paddle connector 152 the peg channel 154 (called-out in FIG. 5). The stiff core 162 can be a polymer, or some other stiff material, that allows for some flex to facilitate functionality (deflection) of the snap ring 160. The flexible overmold 164 can be a pliable material, such as rubber, silicone, latex, or some other like material, for example, to provide comfort to the user when pressing against a rectocele 4 via the vagina 6. When the flexible overmold 164 is narrowed in one direction, it will expand elsewhere, which preserves constant volume of the static paddle 150. The term 'removably fixed' is defined herein as a paddle being fixed to the handle when attached but it can be removed from the handle (such as by a manual operation). Hence, the static paddle 150 can be connected to the handle 102 (via the peg 114), locked in-place (fixed), and then be removed from the handle 102 after use, for example.

Figure 5:
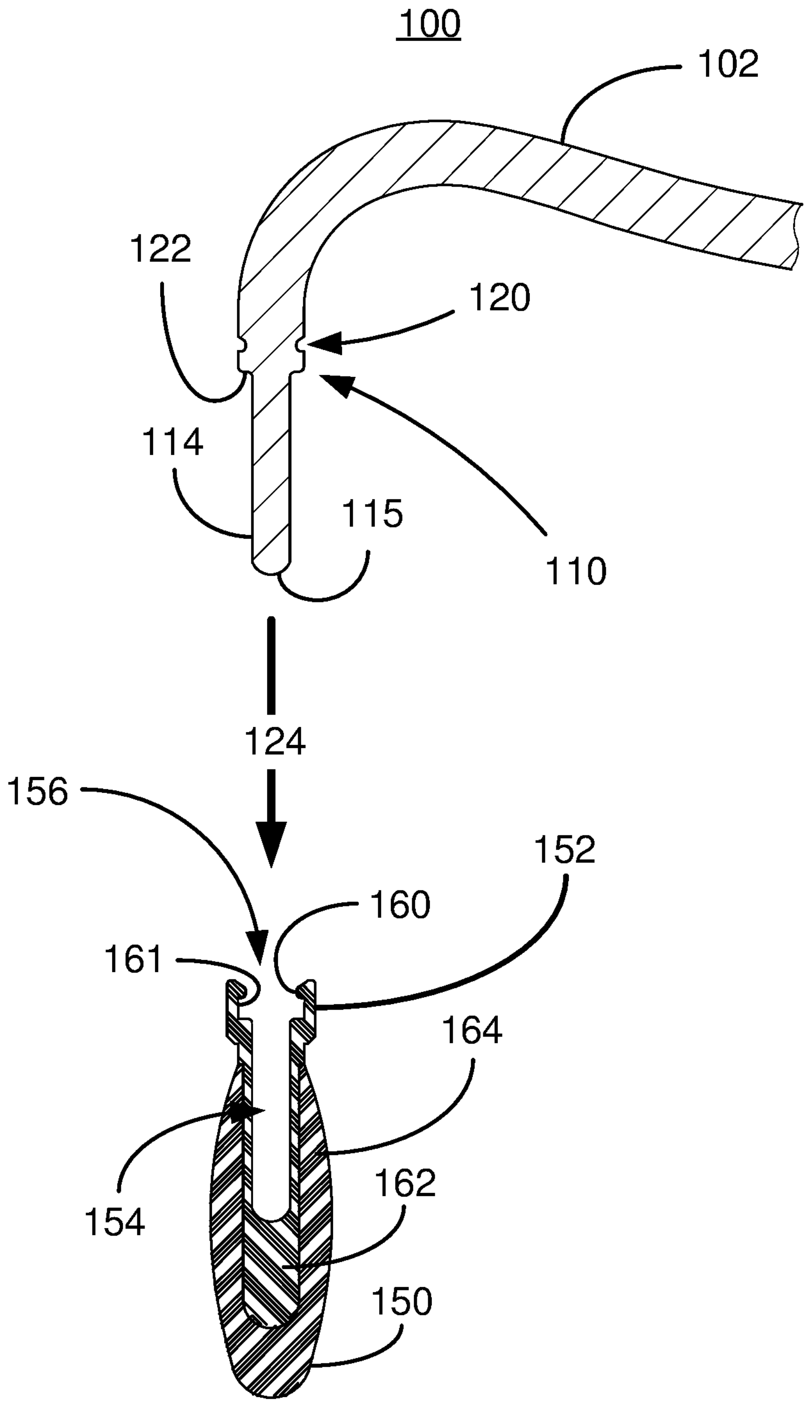
FIG. 5 is a cross-sectional line drawing of an exploded view of the distal region of the rectocele device along cutline A-A consistent with embodiments of the present invention.

FIG. 5 is a cross-sectional line drawing of an exploded view of the distal region of the rectocele device 100 along cutline A-A consistent with embodiments of the present invention. With respect to the rectocele handle 102, the handle distal end 110 generally comprises a snap-ring recess 120 and a handle distal end lip 122 that is defined by the peg 114 being narrower than the rectocele handle side profile width 116. With respect to the static paddle 150, a peg receiving aperture 156 is sized and configured to receive the peg 114 as illustratively shown by the arrow 124. The peg receiving aperture 156 is the opening to the peg channel/cavity 154, which is sized to accommodate the peg 114. In the present embodiment, the static paddle 150 includes a snap-ring 160 and a handle distal end sleeve 161, which are the counterparts to the snap-ring recess 120 and the handle distal end 110 below the snap-ring recess 120. Specifically, when the peg distal end 115 is inserted (arrow 124) into the peg receiving aperture 156, the peg 114 slides towards the bottom of the peg channel 154 until the handle distal end lip 122 deflects the snap-ring 160 outwardly to receive the handle distal end 110. Upon receiving the handle distal end 110, the snap-ring closes around the snap-ring recess 120 when the handle distal end lip 122 reaches (or essentially reaches) the base of the handle distal end sleeve 161. In this way, the static paddle 150 locks on to or otherwise attaches to the handle distal end 110, as shown in FIG. 4B. For reference, the flexible overmold 164 and the stiff (inner) core 162 are shown.

Figure 6A:
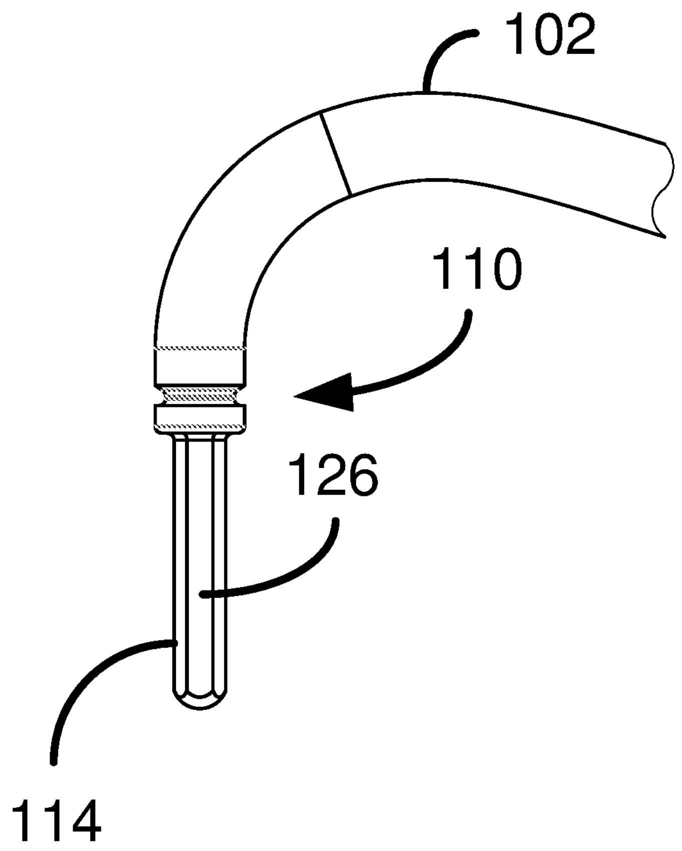
FIGS. 6A and 6B illustratively depict a fixed/anti-rotation peg embodiment system with embodiments of the present invention.
Figure 6B:
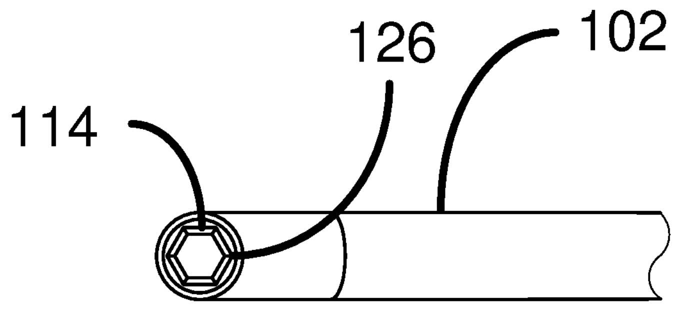

FIGS. 6A and 6B illustratively depict a fixed/anti-rotation peg embodiment system with embodiments of the present invention. As shown in FIG. 6A depicts the distal region of the rectocele handle with the peg embodiment 114 comprising a hexagonal faceted peg sides (key features) 126 that mate with corresponding hexagonal faceted channel sides 168 of the peg channel 154 (see FIG. 7C) thereby preventing rotation of the static paddle 150 when engaged with the faceted peg 114. FIG. 6B illustratively depicts the rectocele handle 102 with the faceted peg 114 pointing out of the page, which unambiguously shows the peg's hexagonally faceted sides 126. Certain other embodiments envision a different number of faceted sides, a key and key channel configuration, or some other kind of anti-rotation feature in the peg 114 or portion of the peg 114. One advantage of the present hexagonal faceted peg embodiment 114 is that the static paddle 150 can be rotated and locked in six different orientations while preventing rotation once the paddle 150 is engaged therewith. Still other embodiments envision no faceted feature or any other anti-rotation feature to prevent rotation whatsoever.

Figure 7A:
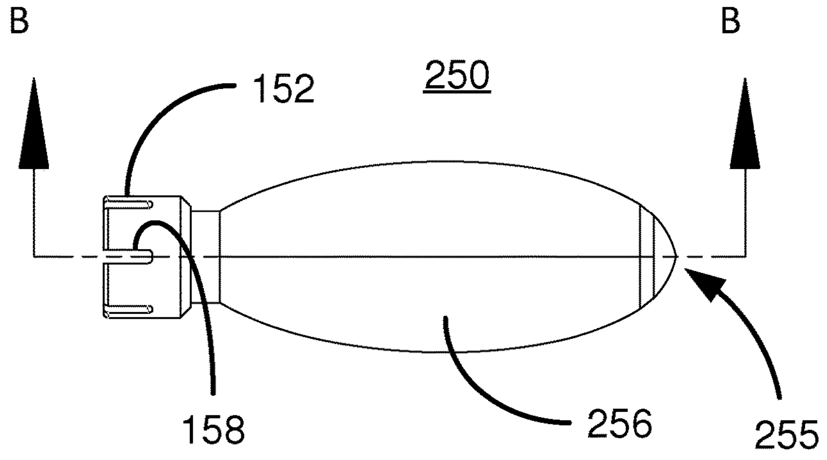
FIGS. 7A-7C illustratively depict line drawings of an alternate static paddle embodiment system consistent with embodiments of the present invention.
Figure 7B:
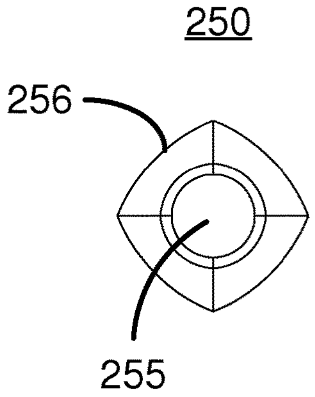
Figure 7C:
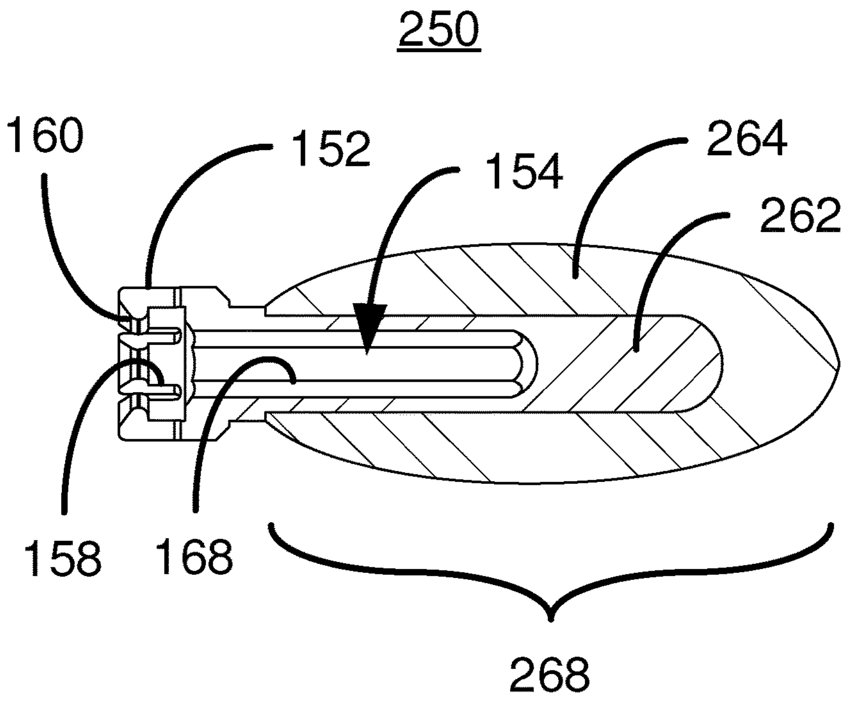

FIGS. 7A-7C illustratively depict line drawings of an alternate static paddle embodiment system consistent with embodiments of the present invention. FIG. 7A is a side view of a static paddle embodiment 250 that is essentially elliptically shaped. The paddle connector 152 (with the expansion slots 158) is more or less identical to that which is shown in the paddle embodiment 150. A cross-section cut-line B-B is presented passing through the center of the paddle connector 152 and static paddle terminal end 255 of the static paddle 250. FIG. 7B depicts the static paddle terminal end 255 extending out of the page. As shown here, the static paddle 250 does not have a smooth profile but rather comprises curved-faceted sides 256.

FIG. 7C illustratively depicts a cross-section of the static paddle 250 along the cut-line B-B of FIG. 7A. The static paddle 250 comprises a hexagonal faceted peg channel 154 in addition to a stiff inner core 262 with a distal paddle portion 268 surrounded/encapsulated by a flexible overmold 264, like the static paddle 150 of FIG. 5. The paddle connector 152 comprises the same snap-ring 160 and expansion slots 158 are those of the static paddle embodiment 150. In this way, the static paddle embodiment 250 provides an optional/different shape to that of the static paddle embodiment 150. Accordingly, an end user can swap out the first shaped static paddle 150 with the second shaped static paddle 250 if that is their preference by simply yanking on the first static paddle 150 causing the paddle connector to open up via the expansion slots 158 and then sliding the second static paddle 250 onto the peg 114 until the snap ring 160 snaps onto the snap-ring recess 120 at the handle distal end 110 (see FIG. 5).

Figure 8A:
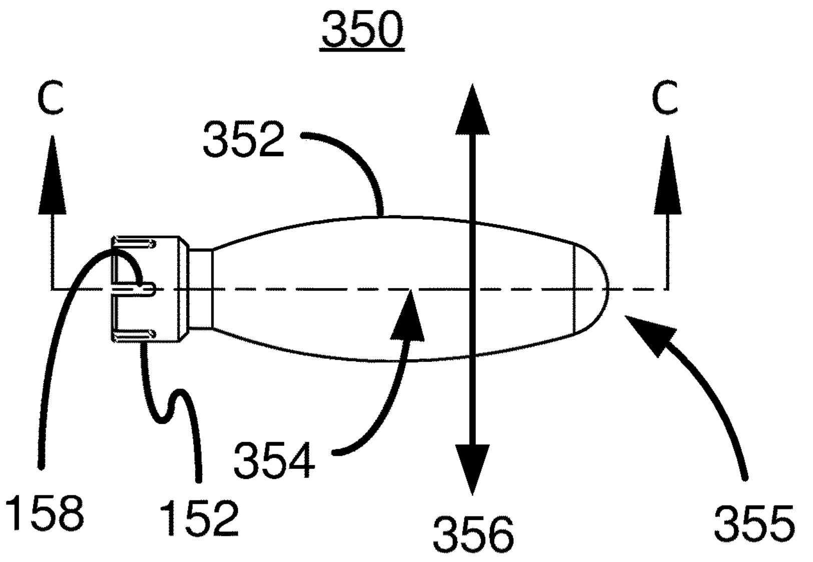
FIGS. 8A-8C illustratively depict line drawings of yet another alternate static paddle embodiment system consistent with embodiments of the present invention.
Figure 8B:
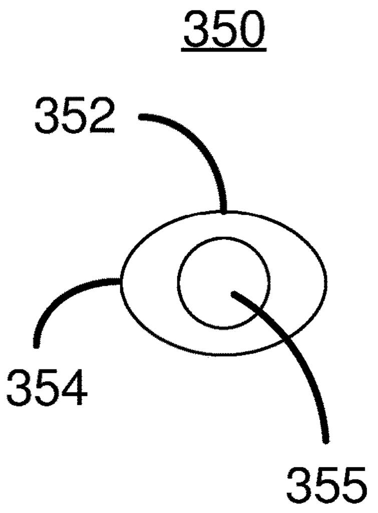
Figure 8C:
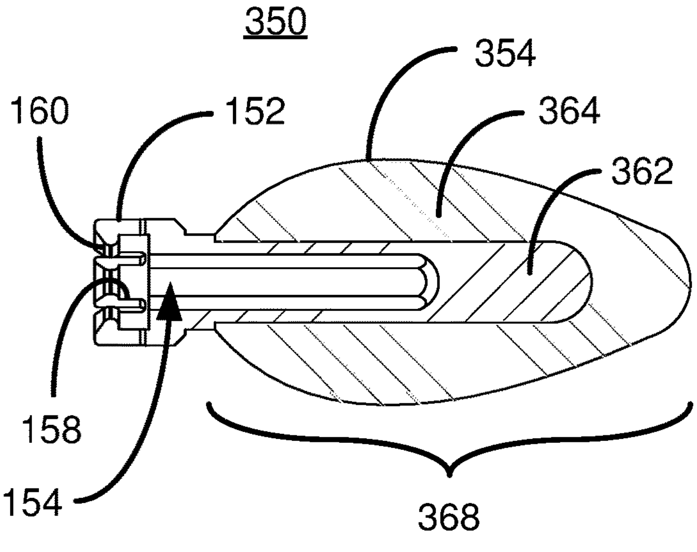

FIGS. 8A-8C illustratively depict line drawings of yet another alternate static paddle embodiment system consistent with embodiments of the present invention. FIG. 8A is a side view of a static paddle embodiment 350 and FIG. 8B is a front view of the static paddle embodiment 350 with the static paddle terminal end 355 extending out of the page. The paddle connector 152 (with the expansion slots 158) is more or less identical to that which is shown in the paddle embodiment 150. A cross-section cut-line C-C is presented passing through the center of the paddle connector 152 and static paddle terminal end 355 of the static paddle 350. As shown in FIG. 8B, the front view of the static paddle embodiment 350 is elliptically shaped along the transverse plane 356 with the largest diameter 354 extending horizontally and the shortest diameter 352 extending vertically.

FIG. 8C illustratively depicts a cross-section of the static paddle 350 along the cut-line C-C of FIG. 8A. The static paddle 350 comprises the hexagonal faceted peg channel 154 in addition to a stiff inner core 362 with a distal paddle portion 368 surrounded/encapsulated by a flexible overmold 364, like the static paddle 150 of FIG. 5. The paddle connector 152 comprises the same snap-ring 160 and expansion slots 158 are those of the static paddle embodiment 150. In this way, the static paddle embodiment 350 provides yet a third optional/different shape to that of the static paddle embodiments 150 and 250. Accordingly, an end user can swap out the first or second shaped static paddle 150 or 250 with the third shaped static paddle 350 if that is their preference.

Figure 9:
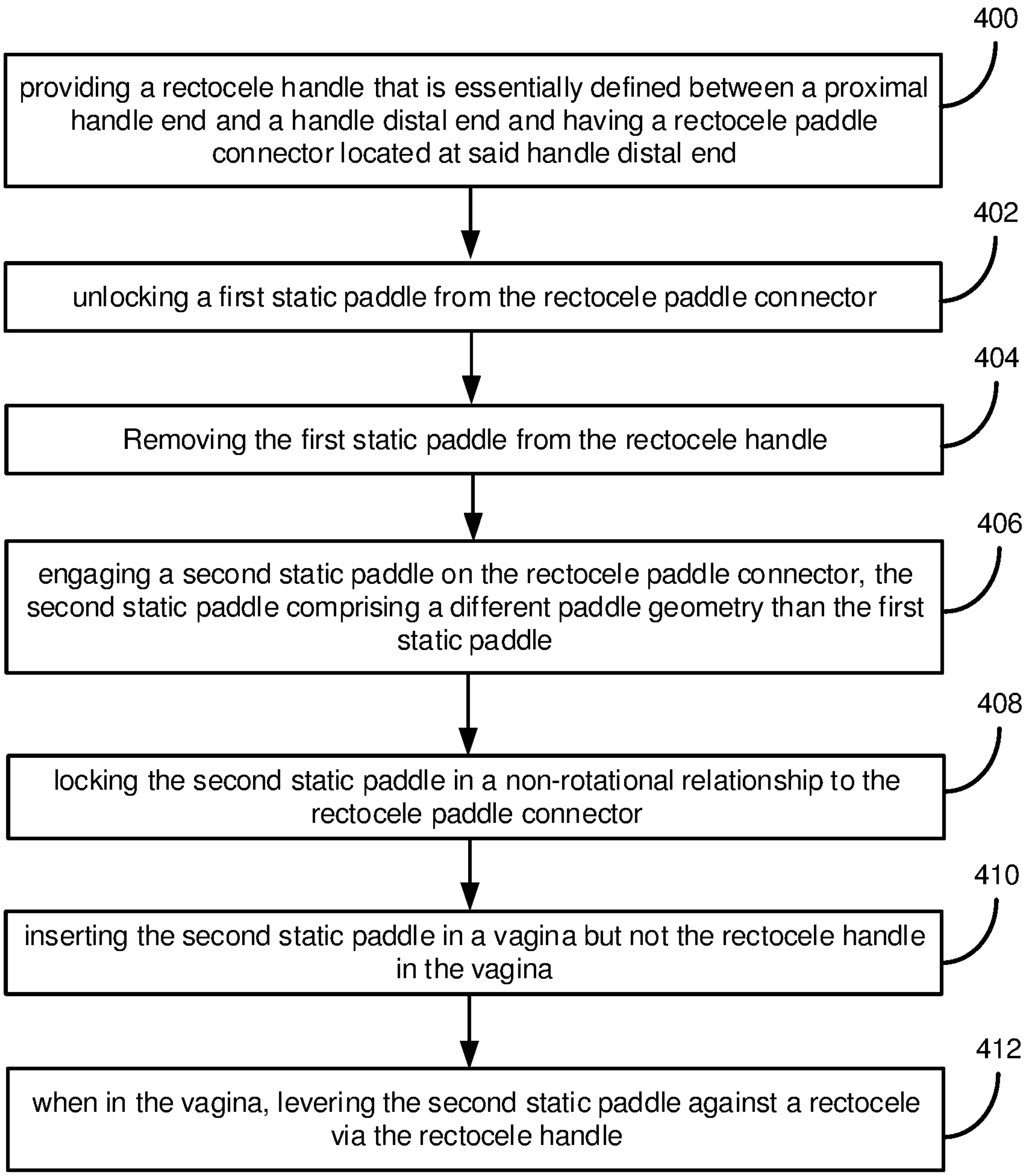
FIG. 9 is a method flowchart of using multiple static paddles with a rectocele handle consistent with embodiments of the present invention.

FIG. 9 is a method flowchart of using multiple static paddles with a rectocele handle consistent with embodiments of the present invention. As featured in step 400, a rectocele handle 102, which is essentially defined between a proximal handle end 112 and a distal handle end 110 and is configured to be gripped by a woman using the rectocele device 100 to press back a rectocele 4 (shown in FIG. 1). The rectocele handle 102 comprises a rectocele paddle connector 118 that is located at the handle distal end 110. The rectocele paddle connector 118 is connected to a first static paddle 150, as shown in FIG. 4B. In certain embodiments discussed above, the first static paddle 150 is connected to the handle distal end 110 via a rectocele paddle connector 118 that generally comprises a snap-ring 160 and handle distal end sleeve 161 that cooperates with a snap-ring recess 120 at the handle distal end 110, which is depicted in FIG. 5.

As featured in step 402, the first static paddle 150 is unlocked from the rectocele paddle connector 118. This could be accomplished by simply grasping and pulling on the first static paddle 150 with enough force to overcome the spring force of the snap-ring 160 thereby disengaging the snap-ring 160 from the snap-ring recess 120.

With the first static paddle 150 unlocked from the rectocele paddle connector 118, remove the first static paddle 150 from the rectocele handle 102, or more specifically the rectocele peg 114, as featured in step 404.

With the first static paddle 150 removed, or otherwise completely separated from the rectocele handle 102 and peg 114, slide a second static paddle 250 (see FIG. 7A) on the peg 114, step 406, and snap the paddle connector 152 to the rectocele paddle connector 118, step 408. The paddle connector 152 when connected to the rectocele paddle connector 118 essentially forms a fixed/engaged relationship between the rectocele handle 102 and the second static paddle 250. The second static paddle 250 is now affixed to the rectocele handle 102 but can be removed from the rectocele handle 102 and replaced with yet a third static paddle 350 (see FIG. 8A). Thus, the nomenclature 'removably affixed' may be used herein to indicate that a static paddle 150 or 250, for example, is affixed to the handle distal end 110 but could be removed to swap out for a different static paddle 350. Certain embodiments of the present invention envision the second static paddle 250 engaging the peg 114 (or more generally the handle distal end 110) in a non-rotational relationship, such as through an anti-rotational feature (e.g., a hexagonal faceted peg 114 and corresponding hexagonal faceted channel 154).

As featured in step 410, with the second static paddle 250 connected to the rectocele handle 102, a user inserts the second static paddle 250 in their vagina 6 just prior to a bowel movement. In certain embodiments, only the second paddle 250 (or portion thereof) is inserted in the women's vagina 6, wherein essentially no part of the rectocele handle 102 is inserted in the vagina 6.

Once in the vagina 6, the user levers the second static paddle 250 against a rectocele while commencing with a bowel movement and then withdraws the second static paddle 250 from the vagina 6 just after the bowel movement, such as within a minute of finishing the bowel movement, step 412.

Other embodiments of the present invention envision the paddle comprising an air/gas pocket that cannot be filled and the volume cannot be changed by an end user. The paddle is envisioned to come with an air pocket by the paddle manufacturer. Because air/gas in an air/gas pocket is technically a compressible fluid, the paddle can change volume (compress but not expand) during use based on changes in pressure when being pressed against a rectocele by an end user. However, despite being compressed, as soon as the air/gas filled paddle is not under pressure from being used, the volume will return to its original shape. Accordingly, such an arrangement is also considered a static paddle because the volume cannot be changed by an end user whatsoever.

With the present description in mind, below are some examples of certain embodiments illustratively complementing some of the methods and apparatus embodiments to aid the reader. The elements called out below in view of the various figures are examples provided to assist in understanding the present invention and accordingly should not be considered limiting.

In that light, as depicted in figures certain embodiment contemplate rectocele device 100 generally comprising a rectocele handle 102 attached to one of several optionally different shaped rectocele paddles 150, 250 or 350. In more detail, the rectocele device 100 can comprise a rectocele handle 102 that is essentially defined between a proximal handle end 112 and a handle distal end 110 and a rectocele paddle connector 118 located at the handle distal end 110. The rectocele device 100 includes a first static paddle 150 removably affixed to the rectocele paddle connector 118 at a paddle connector end 152. A second static paddle 250 is configured to replace the first static paddle 150 after the first static paddle 150 is removed from the rectocele paddle connector 118. The first static paddle 150 is configured and sized to fit within a human vagina 6 wherein the first static paddle 150 is only removable from the handle distal end 110 when the first static paddle 150 is not deployed in the human vagina 6.

Optional embodiments further envision the rectocele device embodiment 100 comprising a peg 114 that extends from the handle distal end 110. The first static paddle 150 and the second static paddle 250 each comprise a peg channel 154 that is configured to accommodate the peg 114 when the first or the second static paddle 150/250 is connected to the rectocele paddle connector 118. This can further be wherein the peg 114 comprises at least one lock-and-key feature that matingly engages an opposite key-and-lock feature in the peg channel 154 that when matingly engaged prevents rotation of the first static paddle 150 relative to the handle distal end 110 when the first static paddle 150 is removably affixed to the rectocele paddle connector 118.

Another embodiment contemplates the rectocele device embodiment 100, whereby the rectocele paddle connector 118 comprises a snap-ring recess 120, the first and the second static paddles 150/250 each comprise a snap-ring 160 that is engaged with the snap-ring recess 120 when the first or the second static paddle 150/250 is removably affixed to the rectocele paddle connector 118. The snap-ring 160 is further envisioned to be spring loaded.

The rectocele device embodiment 100 is further imagined wherein the rectocele paddle connector 118 comprises a snap-ring (like snap-ring 160 but on the rectocele paddle connector 118). The first and the second static paddles 150/250 can each comprise a snap-ring recess (similar to snap-ring recess 120 but on the first and the second static paddles 150/250) that is engaged with the snap-ring when the first or the second static paddle 150/250 is removably affixed to the rectocele paddle connector 118.

Another embodiment of the rectocele device embodiment 100 envisions the first static paddle 150 being shaped differently from the second static paddle 250.

Still another embodiment imagines the rectocele device embodiment 100, whereby the first static paddle 150 comprises a soft rubberized overmold 164 that encompasses a portion of a rigid inner paddle armature 162.

The rectocele device embodiment 100 is further contemplating the handle distal end 110 comprising a first geometry that interfaces against a second geometry at the paddle connector 152 in a rotation locking relationship, the rotation locking relationship between the first geometry and the second geometry prevents rotation of the first static paddle 150 relative to the handle distal end 110 when the first static paddle is removably affixed to the rectocele paddle connector. This can further be wherein the second geometry is a male angled shape that fits in a female angled shape in a mating relationship. Or, optionally, it can further be wherein the first geometry and the second geometry allow for a least two different rotational orientations of the first static paddle

150 relative to the rectocele paddle connector 118 before the first static paddle 150 is removably affixed to the rectocele paddle connector 118.

Still, another embodiment of the present invention contemplates a rectocele managing instrument 100 generally comprising a rectocele handle 102 attached to one of several optionally different shaped rectocele paddles 150, 250 or 350. In this embodiment, the rectocele handle 102 can be gripped by a user's hand, the handle 102 being defined as a rigid or semi-rigid member that extends between a handle proximal end 112 and a handle distal end 110, a rectocele paddle connector 118 located at the handle distal end 110. The rectocele device 100 further comprises a second static paddle 250 that is affixed to the rectocele paddle connector 118, the second static paddle 250 is a replacement of a first static paddle 150 that was affixed to the rectocele paddle connector 118 prior to the second static paddle 250 being connected thereto. The first static paddle 150 is shaped differently than the second static paddle 250. The first static paddle 150 and the second static paddle 250 are configured to fit within a human vagina 6. The first and the second static paddles 150 and 250 are only removable from the handle distal end 110 when not deployed in the human vagina 6.

The rectocele managing instrument embodiment 100 further envisions the first static paddle 150 comprising an air pocket.

The rectocele managing instrument 100 further contemplates the first static paddle 150 and the second static paddle 250 each comprising a stiff inner core 162 with a portion of the stiff inner core 162 covered by a flexible overmold 164.

Another embodiment of the rectocele managing instrument 100 can further include a peg 114 that extends from the handle distal end 110. The first static paddle 150 and the second static paddle 250 each comprise a peg channel 154 that is configured to accommodate the peg 114 when the first or the second static paddle 150/250 is connected to the rectocele paddle connector 118. This can further be wherein the peg 114 comprises at least one lock-and-key feature that matingly engages an opposite key-and-lock feature in the peg channel 154 that when matingly engaged prevents rotation of the first static paddle 150 relative to the handle distal end 110 when the first static paddle 150 is removably affixed to the rectocele paddle connector 118.

In another embodiment of the rectocele managing instrument 100, the rectocele paddle connector 118 can connect to the first static paddle 150 via a relationship involving a snap-ring and snap-ring recess 120.

Another embodiment of the rectocele managing instrument 100 can further be wherein the first static paddle 150 and the second static paddle 250 comprise a volume that essentially cannot be changed.

Still yet another embodiment of the present invention envisions a method that uses a rectocele handle 102 essentially defined as a member that is between a proximal handle end 112 and a handle distal end 110 and having a rectocele paddle connector 118 located at the handle distal end 110. The method steps include unlocking a first static paddle 150 from the rectocele paddle connector 118, the first static paddle 150 is removed from the rectocele handle 102, and a second static paddle 250 is engaged with (on) the rectocele paddle connector 118. The second static paddle 250 comprises a different paddle geometry than the first static paddle 150. After the second static paddle 250 is engaged with the rectocele paddle connector 118, the second static paddle 250 is locked in a non-rotational relationship to the rectocele paddle connector 118. A non-rotational relationship means that when the second static paddle 250 is engaged with the rectocele paddle connector 118 and locked in place, the second static paddle 250 cannot rotate (with relation to the rectocele paddle connector 118). With the rectocele device 100 assembled, next the second static paddle 250 is inserted in a human vagina 6 (by a woman using the rectocele device 100) but not the rectocele handle 102 in the human vagina 6. When in the human vagina 6, the second static paddle 250 can be leveraged against a rectocele 4 via the rectocele handle 102 thereby pushing the rectocele bulge 4 back into the rectum 14 so that the woman 11 can evacuate the bowel more efficiently. The first static paddle 150 is shaped differently from the second static paddle 250.

The above sample embodiments should not be considered limiting to the scope of the invention whatsoever because many more embodiments and variations of embodiments are easily conceived within the teachings, scope and spirit of the instant specification.

It is to be understood that even though numerous characteristics and advantages of various embodiments of the present invention have been set forth in the foregoing description, together with the details of the structure and function of various embodiments of the invention, this disclosure is illustrative only, and changes may be made in detail, especially in matters of structure and arrangement of parts within the principles of the present invention to the full extent indicated by the broad general meaning of the terms in which the appended claims are expressed. For example, although the snap-ring 160 is described as one mechanical element that can be used to fixedly connect the rectocele handle 102 with a paddle 150, a person skilled in the art will appreciate that the snap-ring 160 can be some other kind of snapping mechanism or attaching mechanism known to those skilled in the art to allow for removing one static paddle and reinstalling a different static paddle without departing from the scope and spirit of the present invention. Another example is that although the present embodiments of the static paddle comprise a stiff inner core 162 at least partially surrounded by a flexible overmold 164, it should be appreciated that multiple layers of different stiffness overmold can be incorporated without departing from the scope and spirit of the present invention. Moreover, in certain embodiments, a paddle 150/250/350 can be connected to the distal handle end 110 by way of a threaded fitting, a javelin fitting, a rib and cuff fitting, a clamp fitting, a set screw and cuff fitting, or some other fitting known to those skilled in the art while preserving the functionality described herein. The preferred embodiments described herein are directed to a rectocele device with some application as a cystocele device, which accordingly, is not intended for uses beyond the scope and spirit of addressing a rectocele or cystocele of a woman.

It will be clear that the present invention is well adapted to attain the ends and advantages mentioned as well as those inherent therein. While presently preferred embodiments have been described for purposes of this disclosure, numerous changes may be made which readily suggest themselves to those skilled in the art and which are encompassed in the spirit of the invention disclosed and as defined in the appended claims.

What is claimed is:

1. A device comprising:

a first and a second paddle that are shaped differently, the paddles are configured to be used in a vagina to apply pressure on a rectocele or cystocele;

a handle connected to one of the paddles at a time, wherein at least a majority of the handle is configured to always stay outside of the vagina;

a peg that extends downward from the handle, the first paddle and the second paddle each comprising a peg channel that is configured to accommodate the peg when the first or the second paddle is connected to the handle.

2. The device of claim 1, wherein the handle distal end comprises a first geometry that interfaces against a second geometry at the paddle connector in a locking relationship, the locking relationship between the first geometry and the second geometry prevents rotation of the first paddle relative to the handle distal end when the first paddle is removably affixed to the paddle connector.

3. The device of claim 2, wherein the second geometry is a male angled shape that fits in a female angled shape in a mating relationship.

4. The device of claim 2, wherein the first geometry and the second geometry are configured to allow for a least two different rotational orientations of the first paddle relative to the paddle connector prior to the first paddle removably affixed to the paddle connector.

5. The device of claim 1, wherein the peg comprises at least one lock-and-key feature that matingly engages an opposite key-and-lock feature in the peg channel that when matingly engaged is adapted to prevent rotation of the first paddle relative to the handle when the first paddle is connected to the handle.

6. The device of claim 1, wherein the paddle connector comprises a snap-ring recess, the first and the second paddles each comprise a snap-ring that is engaged with the snap-ring recess when the first or the second paddle is removably affixed to the paddle connector.

7. The device of claim 1, wherein the paddles each comprise a volume that is not increased by an addition of gas.

8. The device of claim 1, wherein the paddle connector comprises a snap-ring, the first and the second paddles each comprise a snap-ring recess that is engaged with the snap-ring when the first or the second paddle is removably affixed to the paddle connector.

9. The device of claim 1, wherein the first paddle is shaped differently from the second paddle.

10. The device of claim 1, wherein the first paddle comprises a rubberized overmold that encompasses a portion of a rigid inner paddle armature.

11. A rectocele and/or cystocele device comprising:

a plurality of different shaped paddles each of which are configured to apply pressure on a rectocele or cystocele from inside a vagina when connected to a handle that is not intended to go inside of the vagina;

a peg that extends from a distal end of the handle and in-line with the handle, the plurality of different shaped paddles each comprising a peg channel that is configured to accommodate the peg when one of the plurality of different shaped paddles is connected to the handle.

12. The rectocele and/or cystocele device of claim 11, wherein each of the plurality of different shaped paddles are connected to the handle in a locking relationship that prevents rotation of the paddle relative to the handle.

13. The rectocele and/or cystocele device of claim 12, wherein each of the plurality of different shaped paddles are configured to be attached to the handle in at least two different rotation positions prior to being locked on the handle.

14. The rectocele and/or cystocele device of claim 11, wherein the plurality of different shaped paddles comprises a first paddle and a second paddle, the second paddle is connected to the handle where the first paddle previously was connected to the handle.

15. The rectocele and/or cystocele device of claim 11, wherein each of the plurality of different shaped paddles comprise a gas pocket that cannot be filled.

16. The rectocele and/or cystocele device of claim 11, wherein each of the plurality of different shaped paddles are static paddles that cannot be filled with gas to increase volume.

17. A method comprising:

providing a set of different shaped paddles, each of the set of different shaped paddles is connectable to a handle, wherein the handle comprises a peg that extends downward from the handle, each of the set of different shaped paddles comprises a peg channel that is configured to accommodate the peg when the each of the set of different shaped paddles are connected to the handle;

connecting a first paddle of the set of different shaped paddles to the handle;

inserting the first paddle in a vagina while essentially holding the handle outside of the vagina;

applying pressure on a rectocele or cystocele from inside a vagina with the first paddle by manipulating the handle.

18. The method of claim 17 further comprising removing the first paddle from the handle and connecting a second paddle of the set of different shaped paddles to the handle.

19. The method of claim 17, wherein none of the set of different shaped paddles can be filled with gas to increase or decrease their respective volume.

* * * * *